(12) United States Patent
Birch et al.

(10) Patent No.: US 10,471,075 B1
(45) Date of Patent: *Nov. 12, 2019

(54) METHODS OF REDUCING RISK OF PRETERM BIRTH

(71) Applicant: AMAG Pharmaceuticals, Inc., Waltham, MA (US)

(72) Inventors: Robert Birch, Saint Charles, MO (US); Michael J. Jozwiakowski, Sudbury, MA (US)

(73) Assignee: AMAG PHARMACEUTICALS, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,941

(22) Filed: Sep. 20, 2017

Related U.S. Application Data

(63) Continuation of application No. 15/143,867, filed on May 2, 2016, now abandoned.

(60) Provisional application No. 62/250,189, filed on Nov. 3, 2015, provisional application No. 62/155,076, filed on Apr. 30, 2015.

(51) Int. Cl.
*A61K 31/573* (2006.01)
*A61K 9/00* (2006.01)

(52) U.S. Cl.
CPC .......... *A61K 31/573* (2013.01); *A61K 9/0014* (2013.01)

(58) Field of Classification Search
CPC .......................... A61K 31/573; A61K 9/0019
See application file for complete search history.

(56) References Cited

U.S. PATENT DOCUMENTS

| | | |
|---|---|---|
| 3,758,687 A | 9/1973 | Ufer et al. |
| 5,906,830 A | 5/1999 | Farinas et al. |
| 6,117,446 A | 9/2000 | Place |
| 6,200,593 B1 | 3/2001 | Place |
| 6,221,379 B1 | 4/2001 | Place |
| 6,241,529 B1 | 6/2001 | Place |
| 6,284,263 B1 | 9/2001 | Place |
| 6,745,962 B2 | 6/2004 | Reed et al. |
| 6,991,191 B2 | 1/2006 | Reed et al. |
| 7,879,360 B2 | 2/2011 | Cunningham et al. |
| 7,884,093 B2 | 2/2011 | Creasy et al. |
| 8,268,352 B2 | 9/2012 | Vaya et al. |
| 8,828,981 B2 | 9/2014 | Creasy et al. |
| 8,951,996 B2 | 2/2015 | Giliyar et al. |
| 9,421,333 B2 | 8/2016 | Wotton et al. |
| 2008/0188829 A1 | 8/2008 | Creasy |
| 2009/0053294 A1 | 2/2009 | Prendergast |
| 2010/0041906 A1 | 2/2010 | Van Boxtel et al. |
| 2010/0278725 A1 | 11/2010 | Liu et al. |
| 2011/0152840 A1* | 6/2011 | Lee .............. A61K 45/06 604/522 |
| 2011/0262502 A1 | 10/2011 | Lee et al. |
| 2014/0271882 A1 | 9/2014 | Giliyar et al. |
| 2014/0303556 A1 | 10/2014 | Travanty |
| 2014/0377317 A1 | 12/2014 | Giliyar et al. |
| 2015/0165049 A1 | 6/2015 | Giliyar et al. |

FOREIGN PATENT DOCUMENTS

| | | | |
|---|---|---|---|
| CN | 103582484 A | 2/2014 | |
| WO | WO-2003/068186 | 8/2003 | |
| WO | WO-2005/044234 A2 | 5/2005 | |
| WO | WO-2005/051401 A2 | 6/2005 | |
| WO | WO-2007/049265 A2 | 5/2007 | |
| WO | WO-2007/114948 A2 | 10/2007 | |
| WO | WO-2008/096122 A2 | 8/2008 | |
| WO | WO-2011/079047 A1 | 6/2011 | |
| WO | WO-2013/016697 A2 | 1/2013 | |
| WO | WO2013016697 | 1/2013 | |
| WO | WO-2013016697 A2 * | 1/2013 | ........... A61K 9/4841 |
| WO | WO-2013/067346 A1 | 5/2013 | |

OTHER PUBLICATIONS

Halpern et al., (Contraception vol. 86 pp. 31-35). Published online Jul. 12, 2013 (Year: 2013).*
Makena Product Page. Clinical Advisor. Published Jun. 30, 2011 (Year: 2011).*
Taylor et al., (Fundamentals of Nursing: The Art and Science of Nursing Care Philadelphia: Lippincott Williams & Wilkins, p. 745-755 published 2011) (Year: 2011).*
Makena: Clinical Advisor (published Jun. 2011) (Year: 2011).*
Halpern et al (Contraception vol. 86, p. 31-35 published Jul. 2013) (Year: 2013).*
Anderson BL et al., (2007) 'Idiopathic Vertebral Abscess in Pregnancy: Case Report and Literature Review,' Am J Perinatology, 24(6):377-9.
Anderson L et al., (2009) 'The Effect of Progesterone on Myometrial Contractility, Potassium Channels, and Tocolytic Efficacy,' Reprod Sci, Jul. 14, 2009 (ePub), 16(11):1052-61.
Anonymous (2008) 'Use of Progesterone to Reduce Preterm Birth,' The American College of Obstetricians and Gynecologists (ACOG) Committee Opinion No. 419, Obstet Gynecol, 112(4):963-5.
Anonymous, (1957). 'New and Nonofficial Remedies—Hydroxyprogesterone Caproate,' Council on Pharmacy and Chemistry (Eds), J Am Med Assoc, 163(5):356-7.
Anonymous, (2008), 'Use of Progesterone to Reduce Preterm Birth,' Committee Opinion No. 419, Committee on Obstetric Practice (Eds), The American College of Obstetricians and Gynecologists, Washington, DC (Publ) (3 pages).
Anonymous, (2006) 'Preterm Birth: Causes, Consequences, and Prevention,' Report Brief • Jul. 2006, Institute of Medicine, Washington, DC (Publ) (4 pages).

(Continued)

*Primary Examiner* — Timothy P Thomas
*Assistant Examiner* — George W Kosturko
(74) *Attorney, Agent, or Firm* — Goodwin Procter LLP

(57) ABSTRACT

This disclosure generally relates to methods for reducing the risk of preterm birth in a pregnant human female patient that include subcutaneous administration of HPC. The disclosure relates in part to the discovery that subcutaneous administration of HPC is actually feasible and can result in sufficient plasma levels of HPC in pregnant patients that can reduce the risk of preterm birth.

9 Claims, 4 Drawing Sheets

(56) References Cited

OTHER PUBLICATIONS

Anonymous, (2006), 'N.48: Asthma,' In: 'The Merck Manual of Diagnosis and Therapy,' (18$^{TH}$ Ed, 2006),<http://scholar.google.com/scholar?q=>, Merck Research Laboratories, NJ, (Publ), XP002630480, ISBN: 0911910182 pp. 381-99, the whole document.
Armstrong J, (2007) '17 Progesterone for Preterm Birth Prevention: A Potential 2 Billion Dollar Opportunity,' Am J Obstet Gynecol, 196(3):194-5.
Bailit JL and Votruba ME, (2007) 'Medical Cost Savings Associated with 17-alpha-Hydroxyprogesterone Caproate,' Am J Obstet Gynecol, 196(3):219.e1-7.
Battaglia FC and Lubchenco LO, (1967) 'A Practical Classification of Newborn Infants by Weight and Gestational Age,' J Pediatr, 71(2):159-63.
Berghella V et al., (2010) '17-alpha-Hydroxyprogesterone Caproate for the Prevention of Preterm Birth in Women with Prior Preterm Birth and a Short Cervical Length,' Am J Obstet Gynecol, 202(4):351.e1-6.
Berghella V, (2009), 'Novel Developments on Cervical Length Screening and Progesterone for Preventing Preterm Birth,' BJOG, 116:182-7.
Bernstein PS, (2008) 'Withdrawal of 17 alpha-Hydroxyprogesterone: A Possible Trigger for Preterm Labor?,' Am J Obstet Gynecol, 198(2):244.
Brancazio LR et al., (2003) 'Prevention of Recurrent Preterm Delivery by 17 alpha-Hydroxyprogesterone Caproate,' N Engl J Med, 349(11):1087-8.
Briery CM et al., (2009) 'Progesterone Does not Prevent Preterm Births in Women with Twins,' South Med J, 102(9):900-4.
Briery CM et al., (2011) 'Women with Preterm Premature Rupture of the Membranes do not Benefit from Weekly Progesterone,' Am J Obstet Gynecol, 204(1):54.e1-5.
Bréart G et al., (1979) 'A Comparative Study of the Efficiency of Hydroxyprogesterone Caproate and of Chlormadinone Acetate in the Prevention of Premature Labor,' Int J Gynaecol Obstet, 16(5):381-4.
Cahill AG et al., (2010), 'Universal Cervical Length Screening and Treatment with Vaginal Progesterone to Prevent Preterm Birth: A Decision and Economic Analysis,' Am J Obstet Gynecol, Jan. 15, 2010 (ePub), 202(6):548.
Cartitis SN et al., (2009) 'Prevention of Preterm Birth in Triplets Using 17-alpha-Hydroxyprogesterone Caproate: A Randomized Controlled Trial,' Obstet Gynecol, 113(2 Pt 1):285-92.
Chao AS et al., (2008) 'Ultrasound Assessment of Cervical Length in Pregnancy,' Taiwan J Obstet Gynecol, 47(3):291-5.
Christian MS et al., (2007) 'Embryo-fetal Toxicity Signals for 17-alpha-Hydroxyprogesterone Caproate in High-Risk Pregnancies: A Review of the Non-Clinical Literature for Embryo-Fetal Toxicity with Progestins,' J Matern Fetal Neonatal Med, 20(2):89-112.
Cnattingius S, (2004) 'The Epidemiology of Smoking During Pregnancy: Smoking Prevalence, Maternal Characteristics, and Pregnancy Outcomes,' Nicotine Tob Res, (6)2:S125-40.
Combs CA et al., (2010) 'Failure of 17-Hydroxyprogesterone to Reduce Neonatal Morbidity or Prolong Triplet Pregnancy: A Double-Blind, Randomized Clinical Trial,' Am J Obstet Gynecol, 203(3):248.e1-9.
Creasy RK and Herron MA, (1981) 'Prevention of Preterm Birth,' Semin Perinatol, 5(3):295-302.
Cypher R, (2007) 'Gestiva for Preventing Prematurity: A New View of an Old Therapy,' Nurs Womens Health,11(3):322-5.
Da Fonseca EB et al., (2003) 'Prophylactic Administration of Progesterone by Vaginal Suppository to Reduce the Incidence of Spontaneous Preterm Birth in women at Increased Risk: A Randomized Placebo-Controlled Double-Blind Study,' Am J Obstet Gynecol, 188(2):419-24.

Davis ME and Plotz EJ, (1957) 'The Metabolism of Progesterone and its Clinical Use in Pregnancy,' Recent Prog Horm Res, 13:347-79.
Davis ME and Wed GL, (1955) '17-alpha-Hydroxyprogesterone-Caproate: A New Substance with Prolonged Progestational Activity; a Comparison with Chemically Pure Progesterone,' J Clin Endocrinol Metab, 15(8):923-30.
Davis ME and Wed GL, (1957) 'Long-Acting Progestational Agents; 17-Ethinyl-19-Nortestosterone Enanthate, 17-alpha-Hydroxyprogesterone Caproate and 17-alpha-Hydroxy-Progesterone Acetate,' Geburtshilfe Frauenheilkd, 17(10):916-28.
Dodd JM et al., (2005) 'Progesterone Supplementation for Preventing Preterm Birth: A Systematic Review and Meta-Analysis,' Acta Obstet Gynecol Scand, 84(6):526-33.
Dodd JM et al., (2013) 'Prenatal Administration of Progesterone for Preventing Preterm Birth in Women Considered to be at Risk of Preterm Birth,' Cochrane Database Syst Rev. Jul. 31, 2013;(7):CD004947.
Doggrell SA, (2003) 'Recurrent Hope for the Treatment of Preterm Delivery,' Expert Opin Pharmacother, 4(12):2363-6.
Dubin N et al., (1979) 'Serum Progesterone and Estradiol in Pregnant Women Selected for Progestagen Treatment,' Int J Fertil, 24(2):86-93.
Durnwald CP et al., (2009) 'The Effect of Treatment with 17-alpha-Hydroxyprogesterone Caproate on Changes in Cervical Length Over Time,' Am J Obstet Gynecol, Aug. 28, 2009 (ePub), 201(4):410.
Durnwald CP et al., (2010) 'Second Trimester Cervical Length and Risk of Preterm Birth in Women with Twin Gestations Treated with 17-α Hydroxyprogesterone Caproate,' J Matern Fetal Neonatal Med, May 4, 2010 (May 4, 2010) (ePub), 23(12):1360-4.
Elovitz MA and Mrinalini C, (2006) 'The Use of Progestational Agents for Preterm Birth: Lessons from a Mouse Model,' Am J Obstet Gynecol, 195(4):1004-10.
Facchinetti F and Vacarro V, (2009) 'Pharmacological Use of Progesterone and 17-alpha-Hydroxyprogesterone Caproate in the Prevention of Preterm Delivery,' Minerva Ginecol, 61(5):401-9.
Facchinetti F et al., (2007) 'Cervical Length Changes During Preterm Cervical Ripening: Effects of 17-alpha-Hydroxyprogesterone Caproate,' Am J Obstet Gynecol, 196(5):453.e1-4.
Facchinetti F et al., (2008) '17-alpha-Hydroxy-Progesterone Effects on Cervical Pro-inflammatory Agents in Women at Risk for Preterm Delivery, Am J Perinatol. Aug. 28, 2008 (ePub), 25(8):503-6.
Facchinetti F et al.,(2005) 'Polyunsaturated Fatty Acids and Risk of Preterm Delivery,' Eur Rev Med Pharmacol Sci, 9(1):41-8.
Facchinetti F, (2010) '17-alpha Hydroprogesterone Caproate and Cervical Changes,' Am J Obstet Gynec, Letters to the Editors, Sep. 2010:e9 (Letter).
Farine D et al., (2008) 'The Use of Progesterone for Prevention of Preterm Birth,' J Obstet Gynaecol Can, 30(1):67-77.
Goldenberg RL et al., (1998) 'The Preterm Prediction Study: The Value of New vs Standard Risk Factors in Predicting Early and all Spontaneous Preterm Births,' Am J Public Health, 88(2):233-8.
Goldstein P et al., (1989) 'A Meta-Analysis of Randomized Control Trials of Progestational Agents in Pregnancy,' Br J Obstet Gynaecol, 96(3):265-74.
Goldzieher J, (1961) 'Symposium on Steroid Hormones. 1. Synthetic Progestational Steroids. Their Significance and Use,' Tex State J Med, 57(12):962-7.
González-Quintero VH et al., (2007) 'Gestational Age at Initiation of 17-Hydroxyprogesterone Caproate (17P) and Recurrent Preterm Delivery,' J Matern Fetal Neonatal Med, 20(3):249-52.
González-Quintero VH et al., (2010) 'Impact of Prior Gestational Age at Preterm Delivery on Effectiveness of 17-alpha-Hydroxyprogesterone Caproate in Practice,' Am J Obstet Gynecol, Aug. 1, 2010 (ePub), 203(3):257.e1-5.
Greene MF, (2003) 'Progesterone and Preterm Delivery—deja vu all Over Again,' N Engl J Med, 348(24):2453-5.
Haas DM and Ramsey PS, (2008) 'Progestogen for Preventing Miscarriage,' Cochrane DB Syst Rev, Apr. 16, 2008 (Apr. 16, 2008), (2):CD003511 (Abstract).
Hartikainen-Sorri A-L et al., (1980), 'Inefficacy of 17-α-Hydroxyprogesterone Caproate in the Prevention of Prematurity in Twin Pregnancies,' Obstet Gynecol, 56(6):692-5.

(56) References Cited

OTHER PUBLICATIONS

Hauth JC et al., (1983) 'The Effect of 17-α-Hydroxyprogesterone Caproate on Pregnancy in an Active Duty Military Population,' Am J Obstet Gynecol, 146(2):187-90.
Henderson ZT et al.,(2009) 'Attitudes and Practices Regarding Use of Progesterone to Prevent Preterm Births,' Am J Perinatol, Mar. 19, 2009 (ePub), 26(7):529-36.
How HY and Sibai BM, (2009) 'Progesterone for the Prevention of Preterm Birth: Indications, When to Initiate, Efficacy and Safety,' Ther Clin Risk Manag, Mar. 26, 2009 (ePub), 5(1):55-64 Epub Mar. 26, 2009.
How HY et al., (2007) 'Prophylaxis with 17-alpha-Hydroxyprogesterone Caproate for Prevention of Recurrent Preterm Delivery: Does Gestational Age at Initiation of Treatment Matter?,' Am J Obstet Gynecol, 197(3):260.e1-4.
Iams JD, (2010) 'Was the Preterm Birth Rate in the Placebo Group too High in the Meis MFMU Network Trial of 17-OHPC?,' Am J Obstet Gynecol, 202(5):409-10.
International Searching Authority, International Search Report (Form ISA/210) for International Application No. PCT/US2010/061078 dated Apr. 28, 2011 (Apr. 28, 2011) (4 pages).
International Searching Authority, Written Opinion of the International Searching Authority International Search Report (Form ISA/237) for International Application No. PCT/US2010/061078 dated Apr. 28, 2011 (Apr. 28, 2011) (12 pages).
Ito K et al., (2001) 'Cigarette Smoking Reduces Histone Deacetylase 2 Expression, Enhances Cytokine Expression, and Inhibits Glucocorticoid Actions in Alveolar Macrophages,' FASEB J, 15(6):1110-2.
Johnson JW et al., (1979) 'High-Risk Prematurity-Progestin Treatment and Steroid Studies,' Obstet Gynecol, 54(4):412-8.
Johnson JW et al.,(1975) 'Efficacy of 17-alpha-Hydroxyprogesterone Caproate in the Prevention of Premature Labor,' N Engl J Med, 293(14):675-80.
Joy S et al., (2010) 'The Risk for Preterm Labor in Women Receiving 17-alpha-Hydroxyprogesterone Caproate Prophylaxis for Preterm Birth Prevention,' Am J Perintol, Dec. 10, 2009 (Oct. 12, 2009) (ePub), 27(4):343-8.
Kauppila A et al., (1980) 'Suppression of Threatened Premature Labor by Administration of Cortisol and 17-alpha-Hydroxyprogesterone Caproate: A Comparison with Ritodrine,' Am J Obstet Gynecol, 138(4):404-8.
Keeler SM et al., (2009) 'A Randomized Trial of Cerclage vs. 17-alpha-Hydroxyprogesterone Caproate for Treatment of Short Cervix,' J Perinat Med, 37(5):473-9.
Keirse MJ, (1990) 'Progestogen Administration in Pregnancy may Prevent Preterm Delivery,' Br J Obstet Gynaecol, 97(2):149-54.
Kessler WB and Borman A,(1958) 'Some Biological Activities of Certain Progestogens. I. 17-alpha-Hydroxyprogesterone 17-n-Caproate,' Ann N Y Acad Sci, 71(5):486-93.
Klebanoff MA, (2007) 'Subgroup Analysis in Obstetrics Clinical Trials,' Am J Obstet Gynecol, 197(2):119-22.
Kuon RJ et al., (2010) 'Pharmacologic Actions of Progestins to Inhibit Cervical Ripening and Prevent Delivery Depend on Their Properties, the Route of Administration, and the Vehicle,' Am J Obstet Gynecol, 202(5):455.e1-9.
Lamont RF and Jayasooriya GS, (2009) 'Progestational Agents for the Prevention of Preterm Birth,' J Perinat Med, 37(1):12-4.
Lee PA et al., (2003) 'International Small for Gestational Age Advisory Board Consensus Development Conference Statement: Management of Short Children Born Small for Gestational Age, Apr. 24-Oct. 1, 2001,' Pediatrics, 111(6 Pt 1):1253-61.
LeVine L, (1964) 'Habitual Abortion. A Controlled Study of Progestational Therapy,' West J Surg Obstet Gynecol, 72:30-6.
Lim AC et al., (2007) 'Progesterone for the Prevention of Preterm Birth in Women with Multiple Pregnancies: The AMPHIA Trial,' BMC Pregnancy Childbirth, 7:7.
Mason MV et al., (2005) '17-alpha-Hydroxyprogesterone Caproate (17P) Usage in a Medicaid Managed Care Plan and Reduction in Neonatal Intensive Care Unit Days,' Manag Care, 14(10):58-63.

Mason MV et al., (2008) 'Optimizing the Use of 17P in Pregnant Managed Medicaid Members,' Manag Care, 17(1):47-52.
Mason MV et al., (2010) 'Impact of 17P Usage on NICU Admissions in a Managed Medicaid Population—A Five-Year Review,' Manag Care, 19(2):46-52.
McCowan LM et al., (2009) 'Spontaneous Preterm Birth and Small for Gestational Age Infants in Women who Stop Smoking Early in Pregnancy: Prospective Cohort Study,' BMJ, Mar. 26, 2009.
Meis PJ and Aleman A, (2004) 'Progesterone Treatment to Prevent Preterm Birth,' Drugs, 64(21):2463-74.
Meis PJ and the Society for Maternal-Fetal Medicine, (2005) '17 Hydroxyprogesterone for the Prevention of Preterm Delivery,' Obstet Gynecol, 105(5 Pt 1):1128-35.
Meis PJ et al., (2005) 'Does Progesterone Treatment Influence Risk Factors for Recurrent Preterm Delivery?,' Obstet Gynecol, 106(3):557-61.
Meis PJ et al., (2003) 'Prevention of Recurrent Preterm Delivery by 17-alpha-Hydroxyprogesterone Caproate,' N Engl J Med, 348(24):2379-85.
Meis PJ, (2006) 'The Role of 17-α-Hydroxyprogesterone Caproate in the Prevention of Preterm Birth,' Women's Health, 2(6):819-24.
Meyerhoff KH et al., (1962) 'The Use of 17-alpha-Hydroxyprogesterone Caproate to Maintain Pregnancy,' Curr Ther Res Clin Exp, 4:499-505.
Northen AT et al., (2007) 'Follow-up of Children Exposed in Utero to 17-alpha-Hydroxyprogesterone Caproate Compared with Placebo,' Obstet Gynecol, 110(4):865-72.
O'Brien JM and Lewis DF, (2009) 'Progestins for the Prevention of Spontaneous Preterm Birth: Review and Implications of Recent Studies,' J Reprod Med, 54(2):73-87.
O'Brien JM et al., (2010) 'Uterine Activity in Women Receiving 17-alpha-Hydroxyprogesterone Caproate for the Prevention of Preterm Birth: An Observational Study,' Am J Perinatol, Jul. 30, 2009 (Jul. 30, 2009) (ePub), 27(2):157-62.
NG SP et al., (2006) 'Hormonal Changes Accompanying Cigarette Smoke-Induced Preterm Births in Mouse Modal,' Exp Biol Med (Maywood), 231(8):1403-9.
O'Brien JM, (2007) 'Progesterone and Preterm Birth,' N Engl J Med, 357(22):2306.
O'Sullivan MD et al., (2005) '17-alpha-Hydroxyprogesterone Caproate Vehicle, Castor Oil, Enhances the Contractile Effect of Oxytocin in Human Myometrium in Pregnancy,' Am J Obstet Gynecol, 202(5):453.e1-4.
Odibo AO et al., (2006) '17-alpha-Hydroxyprogesterone Caproate for the Prevention of Preterm Delivery: A Cost-Effectiveness Analysis,' Obstet Gynecol, 108(3 Pt 1):492-9.
Petrini JR et al., (2005) 'Estimated Effect of 17-alpha-Hydroxyprogesterone Caproate on Preterm Birth in the United States,' Obstet Gynecol, 105(2):267-72.
Rebarber A et al.,(2007) 'Increased Recurrence of Preterm Delivery with Early Cessation of 17-alpha-Hydroxyprogesterone Caproate,' Am J Obstet Gynecol, 196(3):224.e1-4.
Rebarber A et al.,(2010) 'The Use of 17-alpha-Hydroxyprogesterone Caproate (17p) in Women with Cervical Cerclage,' Am J Perinatol, 25(5):271-5.
Rebarber A et al.,(2010) 'Using 17-α-Hydroxyprogesterone Caproate to Impact Rates of Recurrent Preterm Delivery in Clinical Practice,' J Matern Fetal Neonatal Med, 23(10):1139-42.
Reifenstein EC Jr, (1957) 'Introduction of Marked as well as Prolonged Biologic Activity by Esterification; 17-alpha-Hydroxyprogesterone Caproate, a Unique Progestational Compound,' Fertil Steril, 8(1):50-79.
Reijinders FJ et al., (1988) 'Endocrine Effects of 17-alpha-Hydroxyprogesterone Caproate During Early Pregnancy: A Double-Blind Clinical Trial,' Br J Obstet Gynaecol, 95(5):462-8.
Rittenberg C et al., (2007) 'Clinical Characteristics of Women Prescribed 17-alpha-Hydroxyprogesterone Caproate in the Community Setting,' Am J Obstet Gynecol, 197(3):262.e1-4.
Rittenberg C et al., (2008) 'Women Receiving 17-α-Hydroxyprogesterone Caproate Hospitalized for Preterm Labor at Less than 34 Weeks Benefit from Daily Perinatal Nursing Surveillance,' Am J Obstet Gynecol, 199(4):389.e1-4.

(56) References Cited

OTHER PUBLICATIONS

Rittenberg C et al., (2009) 'Preterm Birth Prevention by 17-alpha-Hydroxyprogesterone Caproate vs. Daily Nursing Surveillance,' J Reprod Med, 54(2):47-52.

Rode L et al.,(2009) 'Systematic Review of Progesterone for the Prevention of Preterm Birth in Singleton Pregnancies,' Acta Obstet Gynecol Scand, 88(11):1180-9.

Kautz HD, (1957) 'New and Nonofficial Remedies—Hydroxyprogesterone Caproate,' Council on Pharmacy and Chemistry (Eds), J Am Med Assoc, 163(5):356-7.

Rogers JM, (2009) 'Tobacco and Pregnancy,' Reprod Toxicol, Apr. 9, 2009 (Apr. 9, 2009) (ePub), 28(2):152-60.

Rouse DJ et al., (2007) 'A Trial of 17-alpha-Hydroxyprogesterone Caproate to Prevent Prematurity in Twins,' N Engl J Med, 357(5):454-61.

Sammour MB et al.,(2005) 'Prevention and Treatment of Pregnancy-Induced Hypertension (Preeclampsia) with Progestogens,' J Steroid Biochem Mol Biol, Oct. 19, 2005 (ePub), 97(5):439-40.

Sanchez-Ramos L et al. (2005) 'Progestational Agents to Prevent Preterm Birth: A Meta-Analysis of Randomized Controlled Trials,' Obstet Gynecol, 105(2):273-9.

Schindler AE, (2004) 'First Trimester Endocrinology: Consequences for Diagnosis and Treatment of Pregnancy Failure,' Gynecol Endocrinol, 18(1):51-7 (Abstract).

Schindler AE, (2005) 'Role of Progestogens for the Prevention of Premature Birth,' J Steroid Biochem Mol Biol, Sep. 29 2005 (Sep. 29, 2005)(ePub), 97(5):435-8.

Shahin AY et al., (2009) 'Effect of Oral N-Acetyl Cysteine on Recurrent Preterm Labor Following Treatment for Bacterial Vaginosis,' Int J Gynaecol Obstet, Oct. 11, 2008 (ePub), 104(1):44-8.

Shearman RP and Garrett WJ, (1963) 'Double-Blind Study of Effect of 17-Hydroxyprogesterone Caproate on Abortion Rate,' Br Med J, 1(5326):292-5.

Sibai B et al., (2005) 'Plasma CRH Measurement at 16 to 20 Weeks' Gestation does not Predict Preterm Delivery in Women at High-Risk for Preterm Delivery,' Am J Obstet Gynecol, 193(3 Pt 2):1181-6.

Simhan HN and Caritis SN, (2007) 'Prevention of Preterm Delivery,' N Engl J Med, 357(5):477-87.

Souka AR et al., (1980) 'Therapeutic Value of Indomethacin in Threatened Abortion,' Prostaglandins, 19(3):457-60.

Spong CY et al., (2005) 'Progesterone for Prevention of Recurrent Preterm Birth: Impact of Gestational Age at Previous Delivery,' Am J Obstet Gynecol, 193(3):1127-31.

Spong CY, (2003) 'Recent Developments in Preventing Recurrent Preterm Birth,' Obstet Gynecol, 101(6):1153-4.

Suchowsky G and Junkmann K, (1958) 'Investigations of the Pregnancy-Maintaining Effect of 17-α-Hydroxyprogesterone Caproate in Spayed Pregnant Rabbits,' Acta Endocrinol-COP, 28:129-31.

Suvonnakote T, (1986) 'Prevention of Pre-Term Labour with Progesterone,' J Med Assoc Thailand, 69(10):537-49.

Thornton Jg, (2007) 'Progesterone and Preterm Labor-Still no Definite Answers,' N Engl J Med, 357(5):499-501.

Tita ATN and Rouse DJ, (2009) 'Progesterone for Preterm Birth Prevention: An Evolving Intervention,' Am J Obstet Gynecol, 200(3):219-24.

Tong VT et al., (2013) 'Trends in Smoking Before, During, and After Pregnancy—Pregnancy Risk Assessment Monitoring System, United States, 40 Sites, 2000-2010,' MMWR Surveill Summ, 62(6):1-19.

Varma TR and Morsman J, (1982), 'Evaluation of the Use of Proluton-Depot (Hydroxyprogesterone Hexanoate) in Early Pregnancy,' Int J Gynaecol Obstet, 20(1):13-7.

Velardo JT, (1958) 'Biological Action of 17-α-Hydroxyprogesterone 17-η-Caproate on the Reproductive Process of the Rat,' Annals NY Acad Sci, 71(5):542-54.

Ventolini G et al., (2008) 'The Impact of Maternal Body Mass on the Effectiveness of 17-alpha-Hydroxyprogesterone Caproate,' J Reprod Med, 53(9):667-71.

Vidaeff AC and Ramin SM, (2009) 'Management Strategies for the Prevention of Preterm Birth. Part I: Update on Progesterone Supplementation,' Curr Opin Obstet Gynecol, 21(6):480-4.

Vytiska-Binstorfer E et al., (1986) '[Endocrine Changes Following Progesterone Substitution in Early Pregnancy],' Z Geburtshilfe Perinatol, 190(4):146-8 [Abstract].

Wyatt SN and Rhoads SJ, (2006) 'A Primer on Antenatal Testing for Neonatal Nurses: Part 1. Tests Used to Predict Preterm Labor,' Adv Neonatal Care, 6(4):175-80.

Yemini M et al., (1985) 'Prevention of Premature Labor by 17-alpha-Hydroxyprogesterone Caproate, Am J Obstet Gynecol, 151(5):574-7.

Halpern et al., Contraception, vol. 86, p. 315, Published 2012 (abstract provided).

Makena Product Page, Clinical Advisor, Published online Jun. 30, 2011.

Meis et al., (NEJM Voil. 348, pp. 2379-2385, published 2003).

Abboud, et al. "Effect of Progesterone, Its Hydroxylated and Methylated Derivatives, and Dydrogesterone on Lipid Bilayer Membranes." The Journal of membrane biology (2015): 1-14.

Kuon, et al. "Actions of progestins for the inhibition of cervical ripening and uterine contractions to prevent preterm birth." Facts, views & vision in ObGyn 4.2 (2012): 110.

Proia, et al. "The effect of angiostatic steroids and β-cyclodextrin tetradecasulfate on corneal neovascularization in the rat." Experimental eye research 57.6 (1993): 693-698.

Tripathi, et al. "A competitive immunochromatographic strip assay for 17-α-hydroxy progesterone using colloidal gold nanoparticles." Clinica Chimica Acta 413.1 (2012): 262-268.

Uemura, et al. "Effects of 17. ALPHA.-hydroxyprogesterone on luteinizing hormone release in the rat." Endocrinologia japonica 26.2 (1979): 167-173.

Shaik IH, (2016), 'Route of Administration and Formulation Dependent Pharmacokinetics of 17-Hydroxyprogesterone Caproate in Rats,' Xenobiotica, 46(2): 169-174.

Verma, P, (2010), 'Routes of Drug Administration,' IJPSR, 1(1): 45-59.

Zuidema, J., (1988), 'Release and Absorption Rate Aspects of Intramuscularly Injected Pharmaceuticals,' Int. J. Pharm., 47:1-12.

\* cited by examiner

METHODS OF REDUCING RISK OF PRETERM BIRTH

RELATED APPLICATIONS

This application is a continuation of U.S. Ser. No. 15/143,867, filed on May 2, 2016, which claims priority to and the benefit of U.S. Ser. No. 62/155,076, filed Apr. 30, 2015 and U.S. Ser. No. filed 62/250,189 filed Nov. 3, 2015, each of which is hereby incorporated by reference in its entirety.

BACKGROUND

Preterm delivery is a major health problem in the United States and worldwide. Preterm delivery is often defined as delivery before 37 completed weeks of gestation and has been reported to be the major determinant of infant mortality in developed countries. Preterm delivery is more common in the United States than in many other developed countries, and is predominantly responsible for the relatively high rate of infant mortality in the United States as compared to many other developed countries. Over the past two decades, the rate of preterm delivery in the United States has been reported to have increased from 9% to 11%. In addition to preterm delivery, various other pregnancy-related conditions are major health problems in the United States and worldwide. These include, for example, the delivery of low birth weight neonates, delivery of small for gestational age neonates, pregnancy-related complications, fetal mortality, neonatal morbidity, neonatal mortality, infant morbidity, infant mortality, and childhood developmental delays.

Preterm delivery and other pregnancy-related conditions such as the delivery of low birth weight neonates and/or small for gestational age neonates have serious health, societal, and economic costs. For example, preterm delivery and the delivery of low birth weight neonates and/or small for gestational age neonates can lead to neonatal morbidity, longer stays in the neonatal intensive care unit, and a higher risk of long term morbidities including, for example, cerebral palsy, mental retardation, and learning disabilities.

A number of risk factors for preterm delivery and other pregnancy-related conditions (e.g., previous pregnancy resulting in preterm delivery, previous delivery of low birth weight and/or small for gestational age neonates) have been identified. For example, women who have had a previous spontaneous preterm delivery are at high risk for preterm delivery in subsequent pregnancies. Other risk factors for preterm delivery include: tobacco use during pregnancy (e.g., smoking); infection; multiple gestations (twins, triplets, etc.); alcohol use, abuse, or dependence during pregnancy; substance use, abuse, or dependence during pregnancy; poor nutrition during pregnancy; stress, anxiety, and/or depression; insufficient weight gain during pregnancy; advanced maternal age; African-American descent; and low socio-economic status. Tobacco use or exposure, in particular smoking, during pregnancy is a significant risk factor for preterm delivery and other undesirable maternal, fetal, and neonatal outcomes.

Intramuscular injection of steroids such as 17-alpha-hydroxyprogesterone caproate ("17-HPC" or "HPC") in the gluteus maximus have been used to reduce the risk of preterm birth, but such injections can be painful, and/or may cause the buildup of scar tissue especially since the injection must be repeated weekly for up to 21 weeks. Further, intramuscular injections involve the risk of nerve injury, especially the risk of sciatic nerve injury from dorsogluteal intramuscular injections. There is a need for an alternative route of administration that may, for example, minimize pain and increase the likelihood of patient compliance.

SUMMARY

This disclosure generally relates to methods for reducing the risk of preterm birth in a pregnant human female patient that include subcutaneous administration of HPC. The disclosure relates in part to the discovery that subcutaneous administration of HPC is actually feasible and can result in sufficient plasma levels of HPC in pregnant patients that can reduce the risk of preterm birth.

For example, provided herein is a method of reducing the risk of preterm birth in a pregnant human female patient, comprising subcutaneously administering to said female human patient a dose of a pharmaceutically acceptable viscous non-aqueous liquid formulation comprising hydroxyprogesterone caproate, wherein for example, the dose comprises about 187 mg to about 400 mg, about 200 to about 350 mg, or about 187 to about 350 mg of hydroxyprogesterone caproate (e.g., the dose may be about 250 mg of hydroxyprogesterone caproate, or about 260 mg to about 350 mg, or about 275 mg to about 350 mg of hydroxyprogesterone caproate), or e.g., about 275 mg or about 300 mg. Such disclosed methods result, in some embodiments, in a pharmacologically active plasma concentration of HPC in the patient.

Contemplated methods include subcutaneously administering disclosed doses and/or formulations into the upper anterior thigh or buttocks of the patient, into the upper arm of the patient, and/or into the abdomen of the patient. For example, a method of subcutaneously administering disclosed doses and/or formulation into the triceps area may provide more consistent results (e.g., plasma levels) (e.g., less variability) as compared to subcutaneously administering to other regions of the body. For example, in some embodiments, subcutaneous administration to the triceps area may produce higher blood levels than to administration to the thigh.

Such contemplated methods may include administering a dose about weekly, or every other week, for example, subcutaneously administering about weekly, beginning about 16 weeks or later of gestation. For example, provided methods may include subcutaneous administration of a disclosed dose effective such that the patient after administration has an $AUC_{0-t}$ of about 90%, 80%, or 79% or less, about 75% or less, or about 74% of an $AUC_{0-t}$ as compared to the $AUC_{0-t}$ of a patient administered the same dosage amount of hydroxyprogesterone caproate intramuscularly, and/or upon subcutaneous administration, the patient may have a $C_{max}$ of about 120%, 110%, about 105%, about 100%, or about 90%, 80%, 79% or less, about 70% or less, or about 69% of the $C_{max}$ as compared to the $C_{max}$ of patient administered the same dosage amount of hydroxyprogesterone caproate intramuscularly. In other embodiments, subcutaneous administration in upper arm may result in 10-20% more volume as compared to intramuscular administration.

For example, provided herein in some embodiments, are methods wherein about 24 hours after subcutaneous administration of a 275 mg or a 250 mg dose of hydroxyprogesterone caproate, the human female pregnant patient has a mean plasma concentration of about 3 to about 5 ng/mL, or e.g., about 5 to about 12 ng/mL (e.g., a mean of about 8 ng/mL) e.g., about 24 hours or at about 48 hours or after subcutaneous administration of a 250 mg dose of hydroxyprogesterone caproate, the patient has a mean plasma concentration of about 4 ng/mL hydroxyprogesterone caproate.

For example, provided herein, in some embodiments, are disclosed methods of subcutaneous administration of about four consecutive doses, five consecutive doses, six consecutive doses, or more than six consecutive doses (e.g., doses of compositions as disclosed herein), a human female pregnant patient achieves a mean plasma concentration of about 9 ng/mL or more of the hydroxyprogesterone caproate.

Disclosed methods include subcutaneously administering a dose of a disclosed pharmaceutically acceptable viscous non-aqueous liquid formulation, which may have a volume of about 0.70 mL to about 2 mL, about 1.0 mL, about 1.1 mL, about 1.2 mL, about 1.3 mL, or about 1.4 mL, e.g., a dose of the pharmaceutically acceptable viscous non-aqueous liquid formulation may have a volume of about 1.1 mL to about 1.4 mL, about 1.1 mL to about 1.2 mL or about 1.3 mL to about 1.4 mL, about 1.1 to about 1.3 mL, or about 1.1 mL to about 1.6 mL, or about 1.4 mL. Contemplated doses include doses having a concentration of about 250 mg/mL of the hydroxyprogesterone caproate, or about 260 mg/mL to about 330 mg/mL.

In another embodiment, a method of reducing the risk of preterm birth in a pregnant human female patient is provided, comprising: subcutaneously administering (e.g., into the upper anterior thigh or buttock, upper arm (e.g. triceps area) and/or abdomen) to said female human patient a dose of about 1.0 to about 1.6 mL (e.g., about 1.2 to about 1.4 mL, or about 1.3 to about 1.4 mL) of a pharmaceutically acceptable viscous non-aqueous liquid formulation having a hydroxyprogesterone caproate concentration of about 250 mg/mL. In another embodiment, contemplated methods comprise administering about 1.0 mL of a disclosed pharmaceutically acceptable viscous non-aqueous liquid formulation having a hydroxyprogesterone caproate concentration of about 260 mg/mL to about 330 mg/mL (e.g., about 270 to about 290 mg/mL or about 260 mg/mL to about 300 mg/mL).

Contemplated methods as disclosed herein may include subcutaneous administration to a female human patient of a pharmaceutically acceptable viscous non-aqueous liquid formulation that includes HPC (e.g., 17-α hydroxyprogesterone caproate) and also comprises a pharmaceutically acceptable oil having a viscosity of about 250-1000 cP at 25° C. In some embodiments, a contemplated formulation for use in the disclosed methods is a pharmaceutically acceptable viscous non-aqueous liquid formulation that consists essentially of hydroxyprogesterone caproate, castor oil and benzyl benzoate. In another embodiment, a contemplated dose may have a concentration of 250 mg/mL of hydroxyprogesterone caproate. In a different embodiment, a contemplated dose may have a concentration of about 260 mg/mL to about 310 mg/mL (e.g., about 270 to about 290 mg/mL).

In some embodiments, disclosed methods include subcutaneously administering a dose to a pregnant human female patient beginning between about 16 weeks of gestation, zero days, to about 21 weeks, six days of gestation, and continued until about 37 weeks of gestation or delivery, whichever occurs first. In some embodiments, a pregnant human female patient has a singleton pregnancy. For example, a pregnant human female patient who has a history of singleton spontaneous preterm birth.

In another embodiment, disclosed methods may include subcutaneously administering a first dose of about 260 mg to about 300 mg of hydroxyprogesterone caproate once or twice for a first week, and subcutaneously administering a second dose weekly of about 250 mg to about 260 mg of hydroxyprogesterone caproate. For example, a dose may be administered as a first dose (that e.g., comprises about 250 to about 300 mg of hydroxyprogesterone caproate) twice a week for the first 1 to 2 weeks, and administered weekly thereafter.

BRIEF DESCRIPTION OF THE FIGURES

FIG. 1A depicts a comparison of plasma concentration of hydroxyprogesterone caproate (ng/mL) over 144 hours after administration by IM or SQ injections of 250 mg hydroxyprogesterone caproate contained in 1 mL. FIG. 1B depicts a comparison of plasma concentration of hydroxyprogesterone caproate (ng/mL) over 168 hours after administration by IM (1 mL, 250 mg HPC) or SQ injections into upper arm (triceps area) (1.3 mL, 325 mg hydroxyprogesterone caproate.

DETAILED DESCRIPTION

Figure 1A:
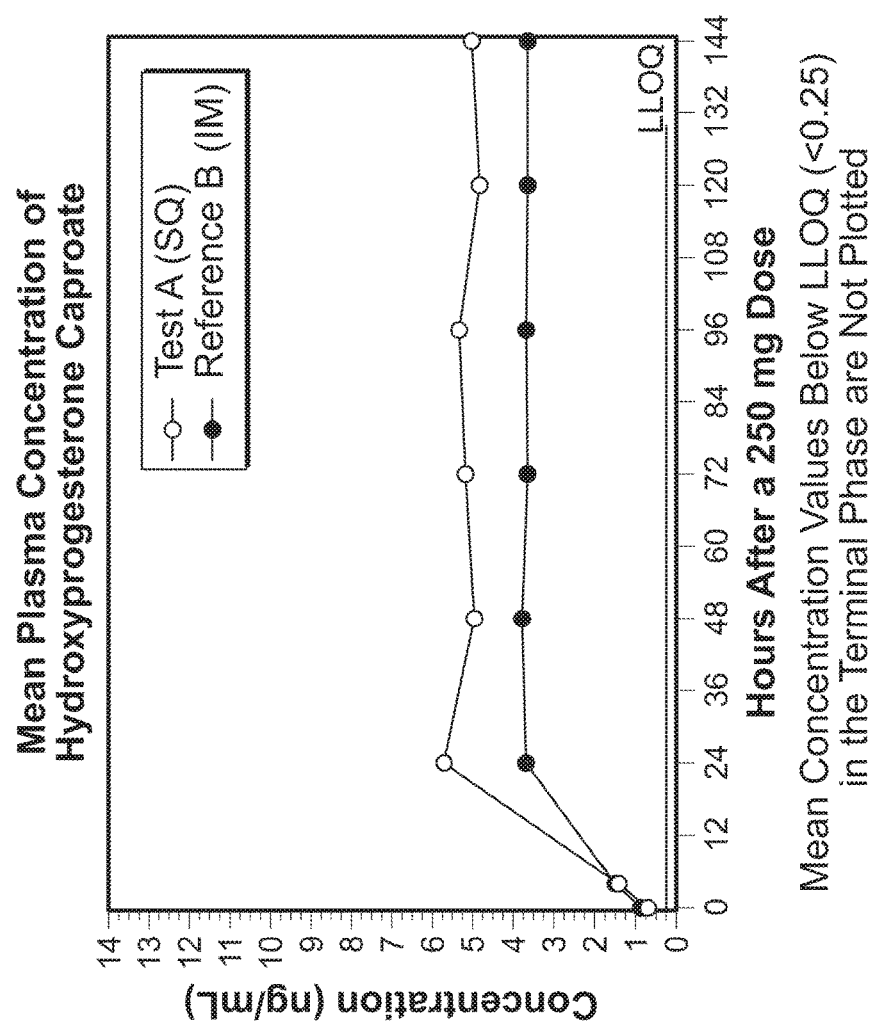
FIG. 1A and FIG. 1B depict the plasma concentration of hydroxyprogesterone caproate after administration.

Described herein are methods for reducing the occurrence of preterm delivery and/or reducing the occurrence of other pregnancy-related conditions such as delivery of low birth weight neonates, delivery of small for gestational age neonates, pregnancy-related complications, fetal mortality, neonatal morbidity, neonatal mortality, infant morbidity, infant mortality, and childhood developmental delays in a human female patient (e.g., a human female patient pregnant with a singleton or with multiple fetuses). For example, methods disclosed herein are effective for reducing the occurrence of preterm delivery in a pregnant human female subject at risk for preterm delivery. Risk factors for preterm delivery and/or other pregnancy-related conditions include previous preterm delivery, exposure to tobacco smoke, exposure to tobacco smoke residue, use of smokeless tobacco, substance use or abuse or dependence, alcohol use or abuse or dependence, stress, anxiety, depression, poor nutritional status, insufficient weight gain during pregnancy, advanced maternal age, low socio-economic status, and combinations thereof. Advantageously, the methods disclosed herein include subcutaneous (SQ) administration of 17-HPC and can provide effective treatment to pregnant human females at risk of e.g. a preterm delivery. SQ injections can be less painful, and/or can involve less risk of complications than IM injections.

A. Preterm Delivery

As noted, preterm delivery is a major health problem in the U.S. and worldwide. Preterm delivery is often defined to include any delivery before 37 weeks or before 35 weeks of gestation. The gestational age of an embryo or fetus may be calculated using ultrasound and/or from the date of the woman's last menstrual period or from 14 days before conception if the date of conception is known. For purposes of determining the effectiveness of the methods of the present invention, preterm delivery can be defined as any live birth occurring prior to 37 weeks of gestation, prior to 36 weeks of gestation, or prior to 35 weeks of gestation. Since viability may occur for live births prior to 35 weeks of gestation, preterm delivery may also be defined as any live birth occurring between 20 and 36 weeks of gestation.

B. Low Birth Weight/Small for Gestational Age Neonates

Contemplated herein in part are methods of reducing the risk of delivering a low birth weight infant in a pregnant human female patient, comprising subcutaneously administering to the patient a dose of hydroxyprogesterone caproate as disclosed herein. Neonates having a relatively low birth weight and/or relatively small size are generally associated with a higher risk of various complications as compared to neonates having a weight and/or size within normal ranges, including an increased risk for neonatal morbidity and mortality, and infant morbidity and mortality. As used herein, the term "low birth weight neonates" encompasses low birth weight neonates (neonates having a weight at birth of less than about 2500 g (about 5.5 pounds)), very low birth weight neonates (neonates having a weight at birth of less than about 1500 g (about 3.3 pounds)), and extremely low birth weight neonates (neonates having a weight at birth of less than about 1000 g (about 2.2 pounds)). A neonate is suitably classified as a small for gestational age neonate if his or her weight at birth is below the 10th percentile for gestational age, as measured according to the accepted standards published by Battaglia et al., or if birth weight and/or length are at least 2 standard deviations (SDs) below the mean for gestational age, as described by Lee et al. See Battaglia et al., *A Practical Classification of Newborn Infants by Weight and Gestational Age*, J. Pediatrics 71(2): 159-63 (August 1967) and Lee et al., *International Small for Gestational Age Advisory Board Consensus Development Conference Statement: Management of Short Children Born Small for Gestational Age, Apr. 24-Oct. 1, 2001*, Pediatrics 111(6 Pt. 1): 1253-61 (June 2003), both of which are incorporated by reference herein for all relevant purposes.

C. Pregnancy-Related Complications

Contemplated herein in an embodiment are methods of reducing the risk pregnancy related complications in a pregnant human female patient, comprising subcutaneously administering to the patient a dose of hydroxyprogesterone caproate as disclosed herein. Pregnancy-related complications contemplated include, for example, placental abruption, placenta previa, and hypertension-related disorders (e.g., preeclampsia and eclampsia). These complications are generally known to contribute to preterm delivery, delivery of low birth weight neonates, etc. Thus, reducing the occurrence of these complications likewise reduces the occurrence of preterm delivery, delivery of low birth weight neonates, etc.

D. Mortality

Contemplated herein are methods of reducing the risk of neonatal mortality in a pregnant human female patient, comprising subcutaneously administering to the patient a dose of hydroxyprogesterone caproate as disclosed herein. Fetal mortality includes any death of a fetus at 20 weeks of gestation or later or any death of a fetus weighing more than 500 g. Fetal mortality includes both antepartum deaths (i.e., deaths occurring before birth) and intrapartum deaths (i.e., deaths occurring during labor and delivery).

Neonatal mortality refers to the death of a live-born neonate within the first 28 days of life. Neonatal mortality includes both early neonatal mortality (i.e., death of a live-born neonate within the first seven days of life) and late neonatal mortality (i.e., death of a live-born neonate after the first seven days of life but within the first 28 days of life). Together, fetal mortality and early neonatal mortality are often referred to as "perinatal mortality." Thus, "perinatal mortality" refers to deaths occurring between 20 weeks of gestation and the end of the 7th day after delivery. Infant mortality includes deaths which occur after 28 days of life, but before one year.

E. Morbidity and Developmental Delays

Also contemplated herein are methods of reducing the risk of neonatal morbidity and/or development delays in a neonate that include subcutaneously administering to a pregnant human female patient a dose of hydroxyprogesterone caproate as disclosed herein. Neonatal morbidity and infant morbidity refer to any disease, disorder, symptom, or other undesirable outcome occurring in a neonate or an infant, respectively. Developmental delays occur when children have not yet reached expected developmental milestones by the expected time period. Neonatal morbidity, infant morbidity, and childhood developmental delays encompass a number of conditions affecting neonates, infants, and/or children, including, but not limited to, transient tachypnea, respiratory distress syndrome, bronchopulmonary dysplasia, a need for ventilatory support/mechanical ventilation, a need for supplemental oxygen, intraventricular hemorrhage, necrotizing enterocolitis, patent ductus arteriosus, retinopathy, sepsis, sudden infant death syndrome (SIDS), cerebral palsy, mental retardation, learning disabilities, and behavioral disorders. Various additional diagnoses associated with neonatal morbidity, infant morbidity, and/or childhood developmental delays include anemia, arthritis, asthma, diabetes, diarrhea, colitis, ear infections, eczema, food or digestive allergies, hay fever, respiratory allergies, seizures, severe headaches or migraines, sickle cell disease, and stuttering and stammering. Other conditions include communication problems, problems with problem solving, attention or learning problems (e.g., attention-deficit hyperactivity disorder (ADHD)), autism, problems carrying out activities and problems with coordination.

II. Risk Factors

An embodiment provided herein is a method of reducing the risk of preterm birth in a pregnant human female patient (e.g., a human female patient that has one or more risk factors (e.g., one or more previous preterm births and/or another risk factor as outlined below)), comprising subcutaneously administering to the patient a dose of hydroxyprogesterone caproate as disclosed herein. A variety of risk factors that may be associated with the above-listed pregnancy-related conditions alone or in combination are detailed below. An exemplary risk factor is a patient that has a history of singleton spontaneous preterm birth. Various risk factors listed below are in connection with exposure to tobacco (e.g., tobacco smoke or tobacco smoke residue). Other risk factors that may contribute to and/or cause one or more pregnancy-related conditions include substance use or abuse or dependence, alcohol use or abuse or dependence, stress, poor nutritional status, insufficient weight gain during pregnancy, advanced maternal age, low socio-economic status, and combinations thereof. Behaviors unfavorable to a subject's health such as smoking tend to cluster (e.g., women who smoke are also more likely to have poor diets). Thus, many women exhibit more than one risk factor for the pregnancy-related conditions, which may increase the risk of occurrence of the pregnancy-related conditions. For example, the occurrence of more than one of the following risk factors are commonly exhibited by a single subject: exposure to tobacco smoke, stress, poor nutritional status, low socio-economic status, alcohol use, abuse, or dependence. Thus, in various preferred embodiments the methods of the present invention are directed to reducing the occurrence of one or more pregnancy-related conditions in a pregnant human female subject exhibiting at least one risk factor selected from the group consisting of exposure to tobacco smoke, stress, poor nutritional status, low socioeconomic status, alcohol use or abuse or dependence, and combinations thereof.

A. Tobacco

One significant risk factor for preterm delivery and the other pregnancy-related conditions is exposure of the pregnant human female to tobacco smoke during pregnancy. This exposure may occur in many forms. Exposure to tobacco smoke includes smoking of tobacco products by the pregnant human female subject herself, as well as passive smoking via the inhalation of smoke from tobacco products used by others (commonly referred to as second-hand smoke or environmental tobacco smoke). In either case, the tobacco smoke may be smoke generated by the use of, for example, a cigarette, a cigar, or a pipe, or any other implement which generates smoke from tobacco. A primary means of exposure of subjects to tobacco smoke in accordance with the present invention is smoking by the pregnant human female subject.

Tobacco smoke residue typically contains nicotine, heavy metals, carcinogens, carbon monoxide, reactive oxygen species, and other toxicants which can contribute to or cause one or more pregnancy-related complications. Exposure to tobacco smoke residue or the use of smokeless tobacco may pose similar risks to the pregnant human female subject as exposure to tobacco smoke. Exposure to tobacco smoke residue includes exposure to toxicants which accumulate on environmental surfaces in areas wherein tobacco products have been smoked. Tobacco smoke residue is commonly referred to as "third-hand smoke." Tobacco smoke residue can accumulate on virtually any environmental surface, including, but not limited to, hair, clothing, furniture, carpeting, and automobile upholstery.

Use of smokeless tobacco is also a risk factor for the above-noted pregnancy-related conditions and includes use of any type of tobacco that is consumed other than by smoking. For instance, smokeless tobacco includes, but is not limited to, dipping tobacco, chewing tobacco, snuff, creamy snuff, snus, tobacco gum, dissolvable tobacco, topical tobacco paste, and tobacco water.

B. Substance Use, Abuse, and/or Dependence

Substance use, abuse, or dependence includes the use or abuse of, or the dependence on, drugs commonly referred to as "street drugs" (e.g., marijuana and cocaine) and/or the use or abuse of, or the dependence on, prescription drugs other than as directed by a physician. Substance use refers to use which is sufficient to result in a positive result on any test commonly used for screening for substance use including, for example, blood tests, urine tests, etc. Substance abuse and substance dependence are suitably diagnosed according to the diagnostic criteria well known to those skilled in the art, such as those set forth in the Diagnostic and Statistical Manual of Mental Disorders (American Psychiatric Association, 4th ed., text revision) (DSM-IV-TR), which is incorporated by reference herein for all relevant purposes. Substance use, abuse, or dependence may suitably refer to the use or abuse of, or the dependence on, for example, opioids, depressants, hallucinogens, stimulants, hypnotics, analgesics, inhalants, sedatives, anxiolytics, or combinations thereof. For instance, substance use, abuse, or dependence may include, but is not limited to, the use or abuse of, or the dependence on, marijuana, cocaine, heroin, methamphetamine, anabolic steroids, 3,4-methylenedioxymethamphetamine (MDMA (ecstasy)), psilocybin, psilocin, lysergic acid diethylamide (LSD), morphine, oxycodone, phencyclidine (also referred to as phenylcyclohexylpiperidine or PCP).

C. Alcohol Use, Abuse, and/or Dependence

Alcohol use, abuse, or dependence generally includes the use or abuse of, or the dependence on, any alcohol-containing product, such as beer, wine, or liquor. Alcohol use may specifically refer to confirmed use of alcohol during pregnancy. High risk alcohol use during pregnancy is defined as confirmed use of alcohol sufficient to produce high blood alcohol levels (100 mg/dL or greater) delivered at least weekly in early pregnancy. Alcohol abuse and alcohol dependency are suitably diagnosed according to the diagnostic criteria well known to those skilled in the art, such as those set forth in the Diagnostic and Statistical Manual of Mental Disorders, which is incorporated by reference herein for all relevant purposes.

D. Stress/Anxiety/Depression

Experiencing relatively high stress levels may put pregnant women at an increased risk for one or more of the above-noted pregnancy-related conditions. Stress levels are suitably measured by a method well known to one skilled in the art, for example, by psychometric scales including the stress component of the Abbreviated Scale for the Assessment of Psychosocial Status in Pregnancy tool, the Stressful Life Events scale (part of the CDC's Pregnancy Risk Assessment and Monitoring System (PRAMS)) and the Modified Life Experiences Survey. A stress level exceeding the pre-defined values for one of these scales would generally be considered to increase the risk for the pregnancy-related conditions discussed above. Stress may be caused, for example, by life events such as divorce, illness, injury, job loss, or the like.

In addition, women who have been diagnosed with anxiety and/or depression according to the standards generally used by medical professionals (e.g., those set forth in the Diagnostic and Statistical Manual of Mental Disorders, which is incorporated by reference herein for all relevant purposes) may also be at increased risk for the pregnancy-related conditions discussed above.

E. Nutritional Status

Poor nutritional status may put a pregnant human female at an increased for the one or more of the above-noted pregnancy-related conditions. Nutritional status may be assessed by weight gain during pregnancy based on pre-pregnancy body mass index (BMI) according to the Institute of Medicine recommendations. See Institute of Medicine, Weight Gain During Pregnancy: Reexamining the Guidelines (2009), which is incorporated by reference herein for all relevant purposes. For example, a pregnant human female subject will generally be considered to have a poor nutritional status if weight gain during pregnancy is insufficient according to these guidelines.

F. Weight Gain

A pregnant human female subject is considered to have gained insufficient weight during pregnancy if the subject had a pre-pregnancy BMI of less than about 18.5 kg/m$^2$ and total weight gain was less than about 12.7 kg (i.e., less than about 28 lbs), had a pre-pregnancy BMI of from about 18.5 to about 24.9 kg/m$^2$ and total weight gain was less than about 11.3 kg (i.e. less than about 25 lbs), had a pre-pregnancy BMI of about 25.0 to about 29.9 kg/m$^2$ and total weight gain was less than about 6.8 kg (i.e., less than about 15 lbs), or had a pre-pregnancy BMI of at least about 30.0 kg/m$^2$ and total weight gain was less than about 5.0 kg (i.e., less than about 11 lbs). Additionally or alternatively, a pregnant human female subject in the second or third trimester is considered to have gained insufficient weight during pregnancy if the subject had a pre-pregnancy BMI of less than about 18.5 kg/m$^2$ and total weight gain during the second and third trimesters was less than about 0.45 kg/week (i.e., less than about 1 lb/week), had a pre-pregnancy BMI of from about 18.5 to about 24.9 kg/m² and total weight gain during the second and third trimesters was less than about 0.36 kg/week (i.e., less than about 0.8 lbs/week), had a pre-pregnancy BMI of from about 25.0 to about 29.9 kg/m² and total weight gain during the second and third trimesters was less than about 0.23 kg/week (i.e., less than about 0.5 lbs/week), or had a pre-pregnancy BMI of at least about 30.0 kg/m² and total weight gain during the second and third trimesters was less than about 0.18 kg/week (i.e., less than about 0.4 lbs/week).

G. Maternal Age

Generally, as maternal age increases so too does the risk of occurrence of preterm delivery and/or one or more other pregnancy-related conditions. By advanced maternal age, it is meant that the pregnant human female subject is at least 35 years of age at the time of delivery.

H. Socio-Economic Status

A pregnant human female subject is suitably considered to have a low socio-economic status if the pregnant human female subject's family and/or household income is at or below the federal poverty level or if the pregnant human female subject is eligible for the Medicaid program III. Steroid Hormones The methods disclosed herein for reducing the occurrence of preterm delivery and/or one or more other pregnancy-related conditions comprise subcutaneous administration of a pharmaceutical composition comprising a steroid hormone. For example, a contemplated progestin for use in the methods disclosed herein is 17-alpha-hydroxyprogesterone or a pharmacologically active derivative or analog thereof. Suitable derivatives of 17-alpha-hydroxyprogesterone include esters of 17-alpha-hydroxyprogesterone, and in particular 17-alpha-hydroxyprogesterone caproate (17-HPC), which has been approved for human use by the United States Food and Drug Administration (FDA). Other esters of 17-alpha-hydroxyprogesterone may also suitably be used. In accordance with various embodiments, contemplated methods include subcutaneous administration of a pharmaceutical composition that comprises 17-HPC.

IV. Administration

Contemplated treatments of a pregnant human female subject with a steroid hormone typically begins during the first or second trimester of pregnancy (i.e., during weeks 1-27 of gestation) and continues until relatively late in the third trimester or until delivery, whichever occurs first. However, it is anticipated that the benefits of the disclosed methods will still be realized even if steroid hormone treatment is not initiated until the third trimester. Thus, for example, treatment with a steroid hormone is typically initiated at between 1 week and about 35 weeks of gestation and continues until about 37 weeks of gestation, or delivery, whichever occurs first. Alternatively, the steroid hormone treatment is suitably initiated at between about 12 weeks and about 30 weeks of gestation and continues until about 36 weeks of gestation, or delivery, whichever occurs first. In some methods of treatment, the steroid hormone treatment is initiated at between about 16 weeks, zero days, to about 21 weeks (or 20 weeks, six days of gestation, or in another embodiment, initiated at about 25 weeks) and continues until about 36 weeks or 37 weeks of gestation, or until delivery of an infant, whichever occurs first. In an embodiment, disclosed methods of treatment, including treatment with a steroid hormone, is initiated during the second or third trimester. Thus, in accordance with various disclosed methods of treatment, subcutaneous treatment with a steroid hormone (e.g., 17-HPC) is initiated at 13 weeks of gestation or later (e.g., at or around 28 weeks of gestation or later).

Disclosed methods include subcutaneous administration of a steroid hormone, e.g., 17-alpha-hydroxyprogesterone caproate (17-HPC). For example, contemplated methods may include administration of a viscous non-aqueous liquid formulation comprising 17-HPC; for example a viscous non-aqueous liquid formulation comprising 17-HPC and a pharmaceutically acceptable oil (e.g., castor oil). In an embodiment, a method of treating a pregnant human female patient in need of reducing the risk of preterm birth is provided comprising subcutaneously administering a formulation comprising 17-HPC and a mixture of non-aqueous solvents such as benzyl benzoate and castor oil. Contemplated formulations may optionally additionally include benzyl alcohol.

Contemplated methods as disclosed herein may include subcutaneous administration of a disclosed composition into e.g., the upper anterior thigh, buttocks, upper arm (e.g., triceps area), or abdomen of the patient.

In various methods of treatment, a disclosed pharmaceutical composition is administered at an interval of once a week or exceeding once per week, for example, administered about weekly beginning about 16 weeks of gestation (e.g., beginning between about 16 weeks, zero days and about 20 weeks, six days of gestation), until about 37 weeks of gestation or until delivery. For example, the pharmaceutical composition may be administered once every other week, once monthly, once every two months, or once every three months. In various other embodiments, the pharmaceutical composition is administered about once weekly, or at an interval of less than one week (e.g., daily or every other day).

In one embodiment, contemplated methods include subcutaneously administering a pharmaceutical composition comprising 17-HPC to a pregnant human female subject on a weekly basis, or more than once a week basis, e.g. subcutaneously administering 17-HPC every 7 days, every 8 days, every 9 days, every 10 days, every 11 days, every 12 days, every 13 days, or every other week. For example, contemplated methods include administering a disclosed pharmaceutical composition that includes 17-HPC and an oil, e.g. castor oil, on an about weekly, or a more-than-once-a-week basis.

Disclosed methods include subcutaneous administration of 17-HPC, wherein upon subcutaneous administration of one, two, three or more doses (e.g., on a weekly basis) the patient has an $AUC_{0-t}$ of about 90%, 80%, 79% or less, about 75% or less, or about 74% (e.g. about 79% to about 74%) as compared to the $AUC_{0-t}$ of a patient administered the same dosage amount of hydroxyprogesterone caproate intramuscularly. Contemplated methods include subcutaneous administration of 17-HPC, wherein upon subcutaneous administration of one, two, three or more doses (e.g., on a weekly basis) the patient has a $C_{max}$ of about 120%, about 110%, about 100%, or, about 90%. 80%, 79% or less, about 70% or less or about 69% (e.g., 79% to 69% or less of the $C_{max}$) as compared to the $C_{max}$ of patient administered the same dosage amount of hydroxyprogesterone caproate intramuscularly.

Subcutaneous administration contemplated herein provides for efficacious plasma levels of 17-HPC in patients. For example, 24 hours after subcutaneous administration of a 250 mg dose of hydroxyprogesterone caproate to a patient as contemplated by methods disclosed herein, the patient has a mean plasma concentration of about 3 to about 5 ng/mL, or about 5-12 ng/mL (e.g., about 7-8 ng/mL) e.g., 24 hours or 48 hours after subcutaneous administration of a 250 mg dose of hydroxyprogesterone caproate. For example, after administration of a 250 mg dose the patient may have has a mean plasma concentration of about 8 ng/mL hydroxyprogesterone caproate.

Subcutaneous administration contemplated herein may provide for efficacious plasma levels of 17-HPC in patients after one or more consecutive doses, for example, after subcutaneous administration of about four consecutive doses, five consecutive doses, six consecutive doses or more than six consecutive doses as disclosed by methods described herein, the patient achieves a mean plasma concentration of about 8 or 9 ng/mL or more of the hydroxyprogesterone caproate.

Pharmaceutical compositions contemplated by methods disclosed herein may include about 100 milligrams (mg) to about 3000 mg of 17-HPC. For example, contemplated methods include administering a pharmaceutical composition that includes 17-HPC and an oil, e.g. castor oil, on a once-monthly basis. Such pharmaceutical compositions may include at least about 100 mg of 17-HPC, at least about 200 mg of 17-HPC, at least about 300 mg of 17-HPC, at least about 400 mg of 17-HPC, at least about 500 mg of 17-HPC, at least about 750 mg of 17-HPC, at least about 1000 mg of 17-HPC, at least about 1500 mg of 17-HPC, at least about 2000 mg of 17-HPC, or at least about 2500 mg of 17-HPC. In accordance with this and various other embodiments, such pharmaceutical compositions may further include less than about 3000 mg of 17-HPC, less than about 2500 mg of 17-HPC, less than about 2000 mg of 17-HPC, less than about 1500 mg of 17-HPC, less than about 1000 mg of 17-HPC, less than about 500 mg of 17-HPC, or less than about 250 mg of 17-HPC.

For example, contemplated compositions for subcutaneous administration as disclosed herein may include compositions having 17-HPC solubilized with a mixture that includes benzyl benzoate and an oil such as castor oil, e.g., solubilized with a mixture having about 53 to about 88 weight percent benzyl benzoate, about 69 to about 88 weight percent benzyl benzoate, or about 63 to about 76 weight percent benzyl benzoate with the remainder castor oil (and optionally benzyl alcohol). Contemplated compositions may include about 21 to about 34 (e.g., about 22 to about 30) weight percent 17-HPC, and an oil such as castor oil, and optionally about 1 to 2 weight percent benzyl alcohol. A contemplated unit dose for example, may have about 1.1 to about 1.3 mg/mL or about 1.0 to about 1.2 mg/mL of 17-HPC.

In another embodiment, contemplated methods include subcutaneously administering a pharmaceutical composition comprising 17-HPC to a pregnant human female subject on a once-weekly basis. For example, contemplated methods include administering a pharmaceutical composition that includes 17-HPC and an oil, e.g. castor oil, on a once-weekly basis. Such pharmaceutical compositions may include at least about 50 mg of 17-HPC, at least about 75 mg of 17-HPC, at least about 100 mg of 17-HPC, at least about 150 mg of 17-HPC, at least about 200 mg of 17-HPC, at least about 250 mg of 17-HPC (e.g., about 260 mg to about 390 mg, e.g. about 260 to about 340 mg, or e.g., 280 mg to about 360 mg or 290 mg to about 380 mg), at least about 500 mg of 17-HPC, at least about 750 mg of 17-HPC, or at least about 1000 mg of 17-HPC. In accordance with this and various other embodiments, such pharmaceutical compositions may further include less than about 1600 mg of 17-HPC, less than about 1500 mg of 17-HPC, less than about 1250 mg of 17-HPC, less than about 1000 mg of 17-HPC, less than about 800 mg of 17-HPC, less than about 500 mg of 17-HPC, or less than about 350 mg 17-HPC. For example, a contemplated method includes subcutaneously administering a pharmaceutical composition comprising 17-HPC to a pregnant human female subject on a once-weekly basis, said pharmaceutical composition suitably including from about 50 mg to about 1600 mg of 17-HPC, from about 100 mg to about 800 mg of 17-HPC, or about 260 to about 350 mg, or about 250 mg 17-HPC.

For example, contemplated methods may include subcutaneously administering a dose of a disclosed pharmaceutically acceptable viscous non-aqueous liquid formulation having about 187 mg to about 400 mg 17-HPC, where the dose has a volume of about 0.70 mL to about 2 mL, about 1.0 mL, about 1.1 mL, about 1.2 mL, about 1.3 mL, or about 1.4 mL, e.g., a volume of about 1.1 mL to about 1.4 mL, about 1.3 mL to about 1.4 mL, about 1.1 mL to about 1.6 mL, about 1.1 to about 1.3 mL, about 1.1 to about 1.2 mL, or about 1.4 mL.

Contemplated herein are methods that include subcutaneous administration of about 1.1 mL to about 1.4 mL (or e.g. 1.0 to 1.2 mL, e.g., 1.1 to 1.2 mL) of a pharmaceutically acceptable viscous non-aqueous liquid formulation having a concentration of about 250 mg/mL of hydroxyprogesterone caproate, or about 260 mg/mL to about 290 mg/mL of 17-HPC.

In still another embodiment, contemplated methods include subcutaneously administering to a pregnant human female subject a first pharmaceutical composition comprising 17-HPC on a once- or twice-weekly basis for 1 to 2 weeks, followed by a second pharmaceutical composition comprising 17-HPC on a once-weekly basis for the remainder of the treatment. In this embodiment, it is contemplated that both the first and second pharmaceutical compositions will include 17-HPC and an oil, e.g. castor oil, and that the first pharmaceutical composition will include an equal or greater amount of 17-HPC than the second pharmaceutical composition. Said first pharmaceutical compositions may include at least about 25 mg of 17-HPC, at least about 50 mg of 17-HPC, at least about 100 mg of 17-HPC, at least about 250 mg of 17-HPC, at least about 500 mg of 17-HPC, at least about 750 mg of 17-HPC, at least about 1000 mg of 17-HPC, at least about 1500 mg of 17-HPC. Said second pharmaceutical compositions may include at least about 25 mg of 17-HPC, at least about 50 mg of 17-HPC, at least about 100 mg of 17-HPC, at least about 250 mg of 17-HPC, at least about 500 mg of 17-HPC, at least about 750 mg of 17-HPC, at least about 1000 mg of 17-HPC, at least about 1500 mg of 17-HPC, for example, wherein the first pharmaceutical composition contains an equal or greater amount of 17-HPC than the second pharmaceutical composition. In accordance with this and various other embodiments, said first pharmaceutical composition may include less than about 1600 mg 17-HPC, less than about less than about 1250 mg of 17-HPC, less than about 1000 mg of 17-HPC, less than about 800 mg of 17-HPC, less than about 500 mg of 17-HPC, or less than about 350 mg 17-HPC. Similarly, said second pharmaceutical composition may include less than about 1600 mg 17-HPC, less than about 1250 mg of 17-HPC, less than about 1000 mg of 17-HPC, less than about 800 mg of 17-HPC, less than about 500 mg of 17-HPC, or less than about 350 mg 17-HPC, wherein the first pharmaceutical composition contains an equal or greater amount of 17-HPC than the second pharmaceutical composition. For example, a contemplated method includes subcutaneously administering to a pregnant human female subject, a first pharmaceutical composition comprising 17-HPC, once- or twice-weekly for one to two weeks, followed by a second pharmaceutical composition comprising 17-HPC once-weekly for the remainder of the treatment. The first pharmaceutical composition may include from about 50 mg to about 1600 mg of 17-HPC, from about 100 mg to about 800 mg of 17-HPC, or about 250 mg 17-HPC. The second pharmaceutical composition may include from about 50 mg to about 1600 mg of 17-HPC, from about 100 mg to about 800 mg of 17-HPC, or about 250 mg 17-HPC wherein the first pharmaceutical composition contains an equal or greater amount of 17-HPC than the second pharmaceutical composition.

Generally, along with the contemplated steroid hormone(s), e.g., 17-HPC, disclosed methods include a pharmaceutical composition that additionally contains one or more pharmaceutically acceptable excipients. For example, provided herein is a pharmaceutically acceptable viscous non-aqueous liquid formulation that includes 17-HPC. For example, the pharmaceutical composition may contain one or more diluents, one or more carriers, one or more solvents, one or more viscosity enhancement agents, one or more buffers, one or more preservatives, one or more dyes, one or more absorption enhancers, and/or one or more biodegradable polymers. For example, contemplated methods include subcutaneously administering a pharmaceutical composition to a pregnant female subject, said pharmaceutical composition comprising 17-HPC and a viscous oil e.g. with a 250-1000 cP at 25° C. In an embodiment, methods disclosed herein include subcutaneous administration of an essentially preservative free pharmaceutical composition that includes 17-HPC and castor oil. For example, methods disclosed herein include subcutaneous administration of a pharmaceutical composition that consists essentially of 17-HPC, castor oil, and benzyl benzoate.

V. Pain Measurement

In an embodiment, disclosed methods that include subcutaneous administration may provide significant pain reduction for the patient being treating, as compared for example to IM administration of 17-HPC. Subcutaneous administration allows for use of shorter needles (e.g., ½" vs 1.5") and narrower gauge needles (27 G vs 21 G). Pain may be measured in any of several ways that will be readily apparently to one of skill in the art. For example, pain may be measured using a Visual Analog Scale (VAS), wherein patients are presented with a horizontal line 100 mm long, representing the pain scale from no pain at one end, to worst possible pain on the other. Patients mark the scale with a vertical line intersecting the horizontal line at the point they believe indicates their level of pain. The distance from 0 to the patient's indicated line is measured in millimeters, which gives a numerical indication of the patient's indicated pain level from 0 to 100.

Alternatively, pain can be using a Numerical Rating Scale (NRS-11) an 11-point scale for patient self-reporting of pain. In the NRS-11, a pain rating of 0 indicates no pain, 1-3 indicate mild pain (pain which is nagging, annoying, but interferes little with activities of daily living (ADLs), 4-6 indicate moderate pain (pain which interferes significantly with ADLs), and 7-10 indicate sever pain (pain which is disabling, and renders the patient unable to perform ADLs).

EXAMPLES

The examples which follow are intended in no way to limit the scope of this invention but are provided to illustrate aspects of the disclosed methods. Many other embodiments of this invention will be apparent to one skilled in the art.

Example 1

An open-label, randomized, single-dose, two-period, two-treatment, four-sequence, crossover study was conducted to compare equal 250 mg doses of 17-HPC injections, 250 mg/ml given as either a 1 mL deep IM injection to the upper outer quadrant of the gluteus maximus or a 1 mL SQ injection to the upper anterior thigh. The study was conducted with 12 healthy, non-tobacco using postmenopausal adult women. The subjects were given the SQ injection in one study period and the IM injection in the other study period according to the four-sequence randomization schedule. Blood was taken at 4, 24, 48, 72, 96, 120 and 144-hours post-treatment, and plasma concentrations of 17-HPC were measured. The interval between doses was 21 days. The analytical data were used to estimate the pharmacokinetic parameters $AUC_{0-t}$, $C_{max}$, and $T_{max}$.

SQ injections of 17-HPC resulted in an average $AUC_{0-t}$ value of 458.5 ng·hr/mL, and average $C_{max}$ value of 4.202 ng/mL. IM injections of 17-HPC resulted in an average $AUC_{0-t}$ value of 620.9 ng·hr/mL, and average $C_{max}$ value of 6.144 ng/mL. $C_{max}$ for SQ injections of 17-HPC was 68.39% $C_{max}$ for IM injections of 17-HPC. $AUC_{0-t}$ for SQ injections of 17-HPC was 73.85% $AUC_{0-t}$ for IM injections of 17-HPC. These results are reported in Table 1, and summarized in FIG. 1A.

| Parameter | Trt | # Datasets | LS Geometric Mean | Contrast (# subjects) | LSGM Ratio (%) | 90% Confidence Interval (%) | ISCV (%) | P-value Period | P-value Sequence |
|---|---|---|---|---|---|---|---|---|---|
| $AUC_{0-t}$ (ng·hr/mL) | A (SQ) | 12 | 458.5 | A vs B (n = 12) | 73.85 | 58.87-92.63 | 31.4 | 0.0004 | 0.7580 |
| | B (IM) | 12 | 620.9 | | | | | | |
| $C_{max}$ (ng/mL) | A (SQ) | 12 | 4.202 | A vs B (n = 12) | 68.39 | 55.80-83.81 | 28.0 | 0.0005 | 0.6284 |
| | B (IM) | 12 | 6.144 | | | | | | |

*Based on data in which concentrations less than the LLOQ of 0.25 ng/mL are set to 0.

Figure 1B:
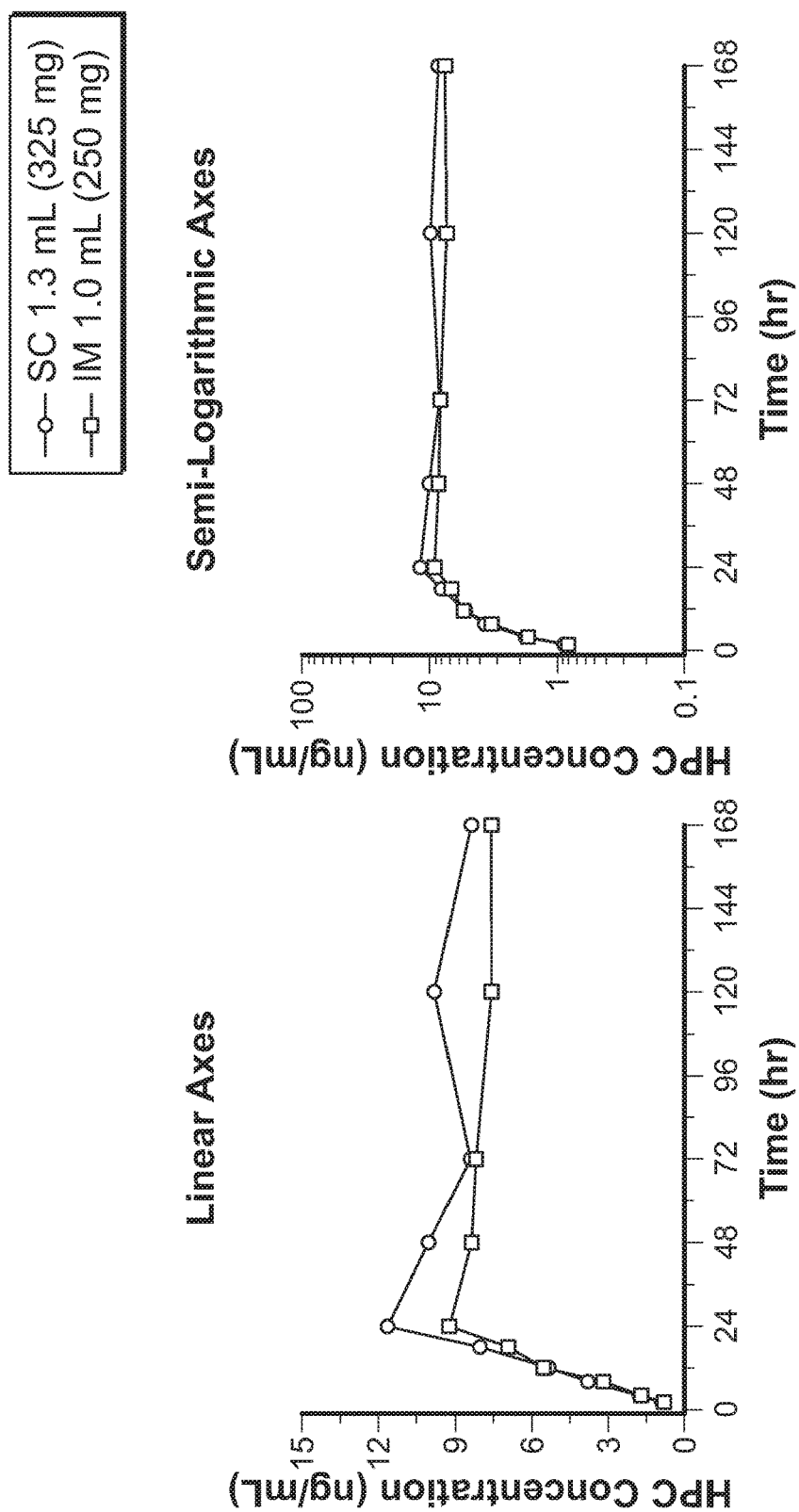

FIG. 1B shows comparative results of administration of plasma concentration of hydroxyprogesterone caproate (ng/mL) over 168 hours after administration by IM (1 mL dose, 250 mg HPC) or SQ injections into upper arm (triceps area) (1.3 mL dose, 325 mg hydroxyprogesterone caproate.

Example 2

An open-label, randomized, single-dose, two-period, two-treatment, four-sequence, crossover study is conducted to compare: A) 17-HPC 250 mg/ml given as a 1 mL deep IM injection to the upper outer quadrant of the gluteus maximus, B) 1 mL SQ 17-HPC 250 mg/ml injection to the upper anterior thigh, C) 17-HPC 250 mg/ml 1 mL SQ 17-HPC 250 mg/ml injection to the upper arm (e.g., triceps area), and D) 17-HPC 250 mg/ml 1.5 mL SQ 17-HPC 250 mg/ml injection to the upper anterior thigh. The study is conducted with 72 healthy, non-tobacco using postmenopausal adult women, 18 per group. Blood is taken pre-dose and at 2, 4, 8, 10, 12, 18, 24, 48, 72, and 120-hours post-treatment and 10, 14, 21, 28, 35 days post-treatment, and plasma concentrations of 17-HPC were measured. The interval between doses was 21 days. The analytical data are used to estimate the pharmacokinetic parameters $AUC_{0-t}$, $C_{max}$, and $T_{max}$.

Example 3

A randomized study is conducted to compare the bioavailability and injection site pain when 17-HPC, 250 mg/mL, is administered as a single 1.0 mL IM injection (250 mg) in the gluteus maximus or a 1.1 (275 mg) or 1.2 mL (300 mg) SQ injection in the triceps area of healthy post-menopausal women. Patients are randomized into two groups by route of administration. Group A receives a 1.0 mL IM injection of 17-HPC into the upper outer quadrant of the gluteus maximus. Group B receives a 1.1 or 1.2 mL SC injection into the upper outer thigh or arm (triceps area). Patient reported outcomes of injection site pain are collected to assess the safety and usability of SQ administration, either by medical staff or for self-administration of 17-HPC. (Patients in Group B can receive a standardized SQ self-administration training from nursing staff that involves verbal instructions and a demonstration of proper use of SQ administration through the use of a standardized script, as well as a review of written patient instructions.) The subcutaneously administered a dose of 17-HPC by medical staff is into the upper triceps area, and/or the anterior abdominal wall, and site personnel conduct and/or observe the procedure.

After injection, patients in groups A and B rate any pain at the injection site with a visual analog scale (VAS), (0 mm=no pain, 100 mm=worst possible pain). Patients in Group B complete an ease-of-use questionnaire, which contains 5 statements that assess the device and the standardized patient training for ease of use by the patient.

Secondary end points include ease-of-use questionnaire scores regarding the device, ease-of-use and training confirmation questionnaire scores regarding written patient instructions and SQ self-administration training, assessment of essential tasks questionnaire scores, self-reported VAS scores for pain at the injection site, and injection-site assessment numeric grades. Injection sites are assessed predose and at 2, 4, 8, 12, 18, and 24 hours postdose. The area around the injection site is evaluated for visual signs such as urticaria, swelling, and bruising, and severity is graded on a scale of 0=none, 1=very slight/barely perceptible, 2=obvious, but well defined, 3=moderate to severe, and 4=severe.

Figure 2:
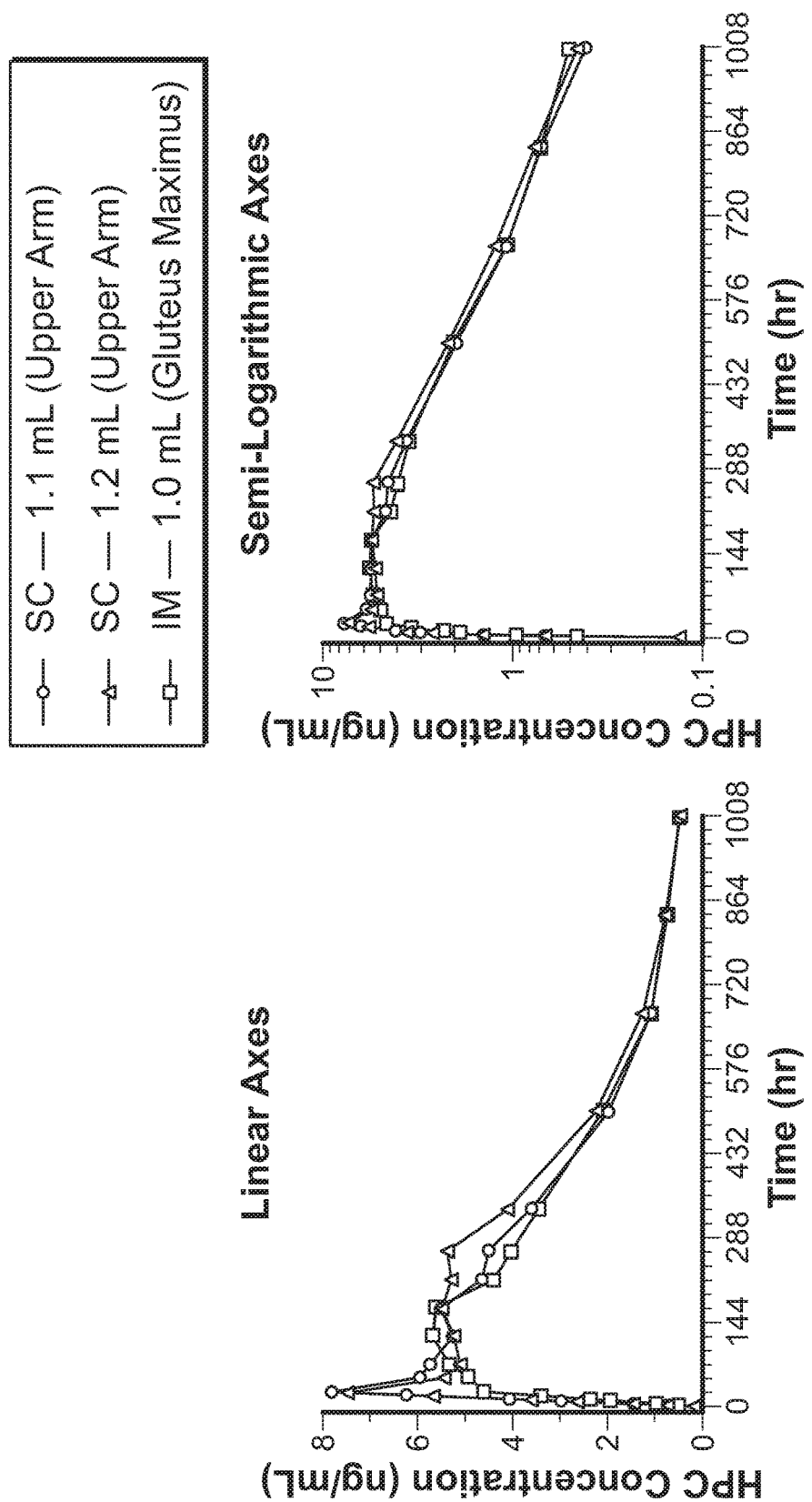
FIG. 2 shows the geometric mean plasma concentrations of HPC after SC and IM—linear (left panel) and semi-logarithmic (right panel).

All patients have blood drawn prior to administration of 17-HPC, and at 2, 4, 8, 12, 18 and 24 hours post dose, and again at approximately the same time as dosing on days 2-7, 14, 21, and 28. Plasma levels of 17-HPC are measured and the analytical data are used to estimate the pharmacokinetic parameters $AUC_{0-t}$, $C_{max}$, and $T_{max}$ through 42 days to assess full profile from absorption through elimination. FIG. 2 shows the geometric mean plasma concentrations of HPC after SC and IM—linear (left panel) and semi-logarithmic-right panel.

Adverse events and medical and surgical history are coded to system organ class and preferred term using the Medical Dictionary for Regulatory Activities version 14.1. An adverse event is considered to be a treatment-emergent adverse event if it starts on or after administration. Vital signs (including heart rate, respiratory rate, and blood pressure) are measured at screening and at 2, 4, 8, 12, 18 and 24 hours post dose.

Table 2 shows results summary of pharmacokinetic parameters for HPC after SC administration 1.1 mL (275 mg) or 1.2 mL (300 mg) in the triceps area of the arm and IM administration of 1.0 mL (250 mg) in the gluteus maximus to healthy postmenopausal female adult subjects.

TABLE 2

| Parameter* | SC (1.1 mL) | SC (1.2 mL) | IM (1.0 mL) |
|---|---|---|---|
| Cmax (ng/ML) | 8.74 (36.3) [17] | 8.13 (37.5) [16] | 7.08 (53.4) [14] |
| Tmax (hr) | 24.0 [17] (18.0-168) | 48.0 [16] (24.0-264) | 120 [14] (24.0-264) |
| AUC (0-t) (hr · ng/ML) | 2,773 (22.6) [17] | 2,938 (24.2) [16] | 2,676 (30.9) [14] |
| AUC (inf) (hr · ng/ML) | 2,935 (22.6) [17] | 3,203 (22.7) [14] | 2,914 (26.5) [11] |
| λz (l/hr) | 0.0031 (26.8) [17] | 0.0031 (38.4) [14] | 0.0031 (37.3) [11] |
| t½ (hr) | 223 (26.8) [17] | 225 (38.4) [14] | 220 (37.3) [11] |

*Geometric mean (geometric CV [N] except Tmax for which the median [N] (range) is reported.

Table 3 shows the statistical comparison of pharmacokinetic parameters for HPC after SC administration of 1.1 mL (275 mg) or 1.2 mL (300 mg) in the arm and IM administration of 1.0 mL (250 mg) in the gluteus maximus to healthy postmenopausal female adult subjects.

TABLE 3

| Parameter | Least Squares Geometric Means Test | Reference | Estimate | Least Squares Geometric Mean Ratio (%) 90% Confidence Interval | | Power* (%) |
|---|---|---|---|---|---|---|
| SC (1.1 mL) vs. IM (1.0 mL) | | | | | | |
| Cmax | 8.74 | 7.08 | 123.42 | 96.55 | 157.77 | 64.9 |
| AUC (0-t) | 2,733.28 | 2,675.96 | 103.64 | 88.83 | 120.91 | 63.7 |
| AUC (inf) | 2,934.58 | 2,913.81 | 100.71 | 86.49 | 117.28 | 64.2 |
| SC (1.2 mL) vs. IM (1.0 mL) | | | | | | |
| Cmax | 8.13 | 7.08 | 114.81 | 89.51 | 147.27 | 65.2 |
| AUC (0-t) | 2,937.70 | 2,675.96 | 109.78 | 93.90 | 128.35 | 63.2 |
| AUC (inf) | 3,202.63 | 2,913.81 | 109.91 | 93.80 | 128.80 | 62.7 |
| SC (1.1 mL) vs. SC (1.2 mL) | | | | | | |
| Cmax | 8.74 | 8.13 | 107.50 | 84.82 | 136.24 | 64.0 |
| AUC (0-t) | 2,733.28 | 2,937.70 | 94.40 | 81.35 | 109.54 | 65.2 |
| AUC (inf) | 2,934.58 | 3,202.63 | 91.63 | 79.50 | 105.61 | 67.5 |

*Power to detect at 20% at 0.05.

Example 4

Formulations

Table 4 shows formulations of HPC solubilized with various ratios of benzyl benzoate (BB)/castor oil (CO) with and without benzyl alcohol (BA) at 5, 5, 15, 25 C over 5 days. The solubility data is fairly constant over multiple days. Weight percent of BB is relative to the castor oil.

| Temp (° C.) | Wt % BB | Avg. HPC wt % | mg HPC/mL solution |
| --- | --- | --- | --- |
| 5° | 53.01 | 18.60 | 200 |
|  | 63.33 | 20.31 | 222 |
|  | 69.43 | 21.62 | 238 |
|  | 75.59 | 23.00 | 253 |
|  | 81.79 | 24.65 | 273 |
|  | 87.91 | 25.22 | 284 |
| 15° | 53.01 | 20.49 | 220 |
|  | 63.33 | 22.96 | 254 |
|  | 69.43 | 24.28 | 269 |
|  | 75.59 | 25.97 | 289 |
|  | 81.79 | 27.32 | 306 |
|  | 87.91 | 28.30 | 320 |
| 25° | 53.01 | 24.08 | 262 |
|  | 63.33 | 27.17 | 303 |
|  | 69.43 | 28.76 | 321 |
|  | 75.59 | 30.62 | 347 |
|  | 81.79 | 31.98 | 363 |
|  | 87.91 | 33.26 | 382 |

Figure 3:
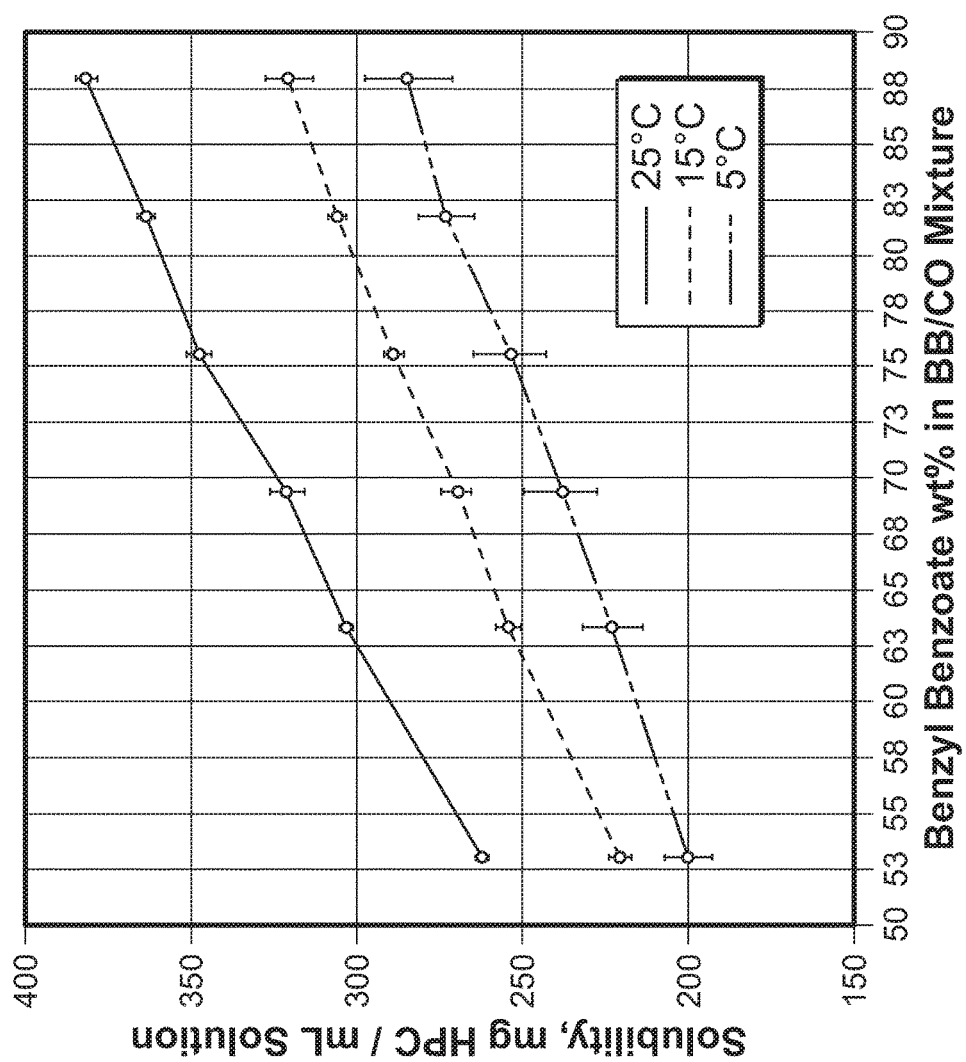
FIG. 3 shows the solubility of 17-HPC in different benzyl benzoate ratios.

FIG. 3 shows the solubility of 17-HPC with a mixture of different ratios of BB and castor oil.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention an and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of reducing the risk of preterm birth in a pregnant human patient, comprising:
   subcutaneously administering to the posterior portion of the upper arm of the pregnant human patient a 1.1 mL dose comprising a pharmaceutically acceptable viscous non-aqueous liquid formulation comprising 275 mg 17-α hydroxyprogesterone caproate, castor oil, and benzyl benzoate,
   wherein the dose is subcutaneously administered weekly, beginning about 16 weeks or later of gestation.

2. The method of claim 1, wherein the dose is subcutaneously administered beginning between about 16 weeks, zero days of gestation to about 20 weeks, six days of gestation, and continued until about 37 weeks of gestation or until delivery, whichever occurs first.

3. The method of claim 1, wherein the pregnant human patient has a singleton pregnancy.

4. The method of claim 3, wherein the pregnant human patient has a history of singleton spontaneous preterm birth.

5. A method of reducing the risk of preterm birth in a pregnant human patient, comprising:
   subcutaneously administering to the posterior portion of the upper arm of the pregnant human patient 1.1 mL of a dose comprising a pharmaceutically acceptable non-aqueous liquid formulation comprising 275 mg 17-α hydroxyprogesterone caproate, castor oil, and benzyl benzoate, and
   wherein the dose is subcutaneously administered once weekly, beginning between about 16 weeks, zero days of gestation to about 20 weeks, six days of gestation, and continued until about 37 weeks of gestation or until delivery, whichever occurs first, and
   wherein the pregnant human patient has a singleton pregnancy and a history of singleton spontaneous preterm birth.

6. The method of claim 1, wherein the pharmaceutically acceptable viscous non-aqueous liquid formulation consists essentially of 17-α hydroxyprogesterone caproate, castor oil, and benzyl benzoate.

7. The method of claim 1, wherein the dose is subcutaneously administered beginning between about 16 weeks to about 21 weeks of gestation, and continued until about 37 weeks of gestation or until delivery, whichever occurs first.

8. The method of claim 1, wherein the dose is subcutaneously administered once weekly.

9. The method of claim 5, wherein the pharmaceutically acceptable non-aqueous liquid formulation consists essentially of 17-α hydroxyprogesterone caproate, castor oil, and benzyl benzoate.

* * * * *